(12) United States Patent  
Levy et al.

(10) Patent No.: US 7,507,241 B2
(45) Date of Patent: Mar. 24, 2009

(54) EXPANDABLE BONE DEVICE

(75) Inventors: Mark M. Levy, Raanana (IL); Ilan Greenberg, Haifa (IL)

(73) Assignee: Expanding Orthopedics Inc., Caesarea Industrial Park (IL)

( * ) Notice: Subject to any disclaimer, the term of this patent is extended or adjusted under 35 U.S.C. 154(b) by 674 days.

(21) Appl. No.: 10/816,809

(22) Filed: Apr. 5, 2004

(65) Prior Publication Data

US 2005/0228391 A1      Oct. 13, 2005

(51) Int. Cl.
*A61B 17/56* (2006.01)
(52) U.S. Cl. ........................................................ 606/60
(58) Field of Classification Search ........... 606/63, 606/90, 198, 205–208, 60, 113, 114, 128, 606/191, 200, 225, 237, 151; 623/16.11–17.11; 600/222
See application file for complete search history.

(56) References Cited

U.S. PATENT DOCUMENTS

| 5,456,667 A | * | 10/1995 | Ham et al. ................... 604/107 |
| 5,685,826 A | * | 11/1997 | Bonutti ....................... 600/204 |
| 5,695,515 A | * | 12/1997 | Orejola ........................ 606/191 |
| 6,127,597 A |   | 10/2000 | Beyar et al. |
| 6,554,833 B2 | * | 4/2003 | Levy et al. ..................... 606/63 |
| 6,582,451 B1 | * | 6/2003 | Marucci et al. ............. 606/207 |
| 6,736,818 B2 | * | 5/2004 | Perren et al. .................. 606/63 |
| 7,087,055 B2 | * | 8/2006 | Lim et al. ...................... 606/61 |
| 2002/0068939 A1 |   | 6/2002 | Levy et al. |
| 2005/0113836 A1 | * | 5/2005 | Lozier et al. .................. 606/80 |

FOREIGN PATENT DOCUMENTS

WO       00/44319       8/2000

\* cited by examiner

*Primary Examiner*—Eduardo C. Robert
*Assistant Examiner*—Michael J Araj
(74) *Attorney, Agent, or Firm*—Dekel Patent Ltd.; David Klein

(57) ABSTRACT

An expandable bone device including a unitary body extending along a longitudinal axis and including a deformable distal end portion having a collapsed orientation for placement adjacent a spinal structure, the deformable distal end portion including relatively wide, mutually contiguous support surfaces outlined by relatively narrow cutouts, the support surfaces being contiguous with the rest of the unitary body via relatively narrow deformable splines, the deformable distal end portion having an expanded orientation wherein the support surfaces are moved transversely outwards away from and generally parallel to the longitudinal axis, and an actuator coupled to the deformable distal end portion and operative to cause movement of the deformable distal end portion between the collapsed orientation and the expanded orientation.

15 Claims, 7 Drawing Sheets

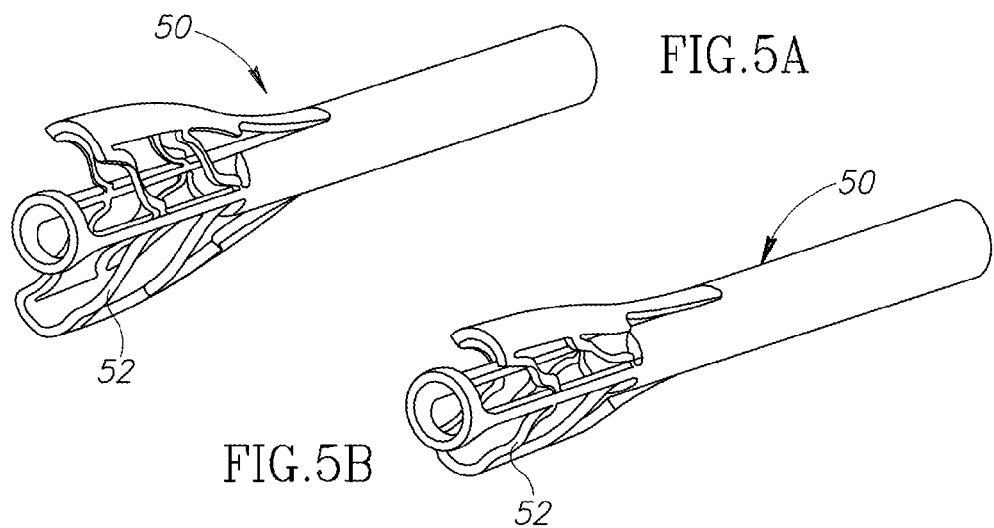
FIG.5A
FIG.5B
FIG.5C
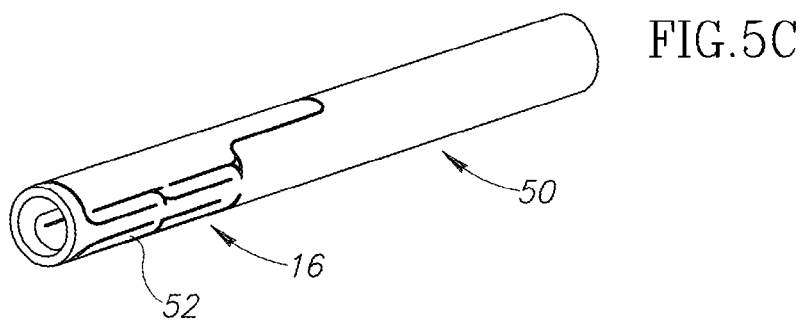
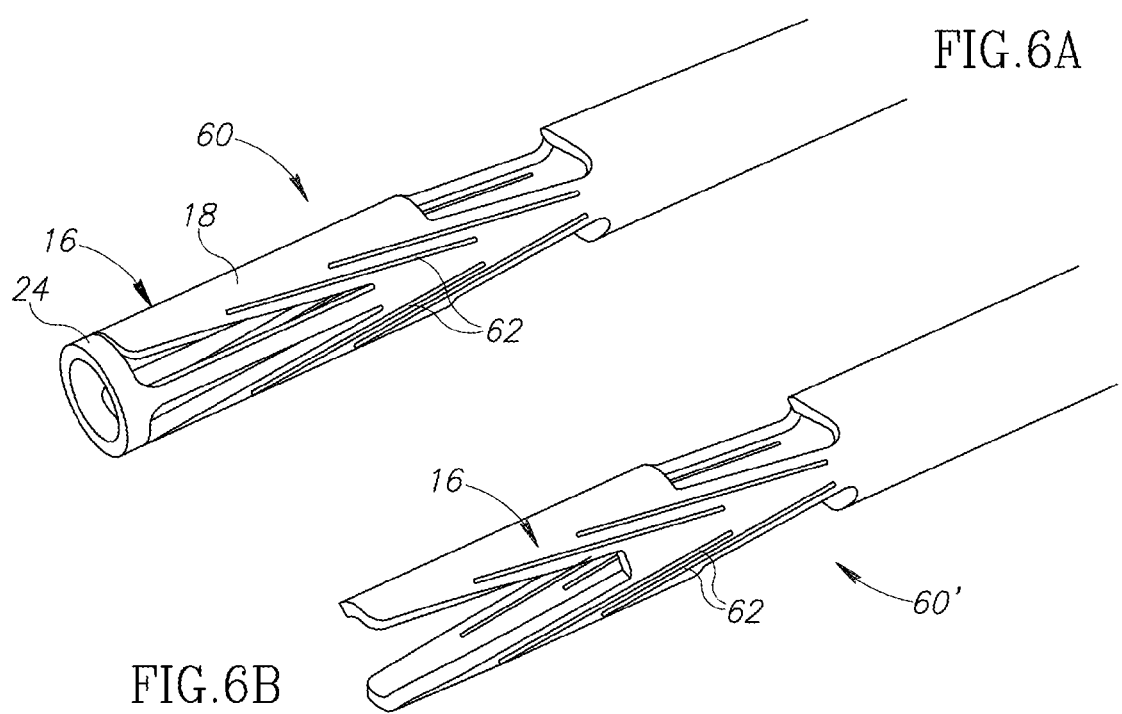
FIG.6A
FIG.6B

EXPANDABLE BONE DEVICE

FIELD OF THE INVENTION

The present invention relates generally to expandable bone devices, such as but not limited to, devices for vertebral body reconstruction (vertebroplasty), such as for treatment of compression fractures of the thoracic and lumbar spine area, or for an expandable bone device for transversely displacing structures associated with the spine, for example.

BACKGROUND OF THE INVENTION

Various instruments and methods for the treatment of compression-type bone fractures and other osteoporotic and/or non-osteoporotic conditions have been developed. In one method, a cavity may be formed in the bone to be treated, followed by the insertion of an inflatable balloon-like device into the bone cavity. Inflation of the balloon-like device causes a compaction of the cancellous bone and/or bone marrow against the inner cortical wall of the bone, thereby resulting in enlargement of the bone cavity and/or reduction of the compression fracture. The balloon-like device is then deflated and removed from the bone cavity. A biocompatible filling material, such as methylmethacrylate cement or a synthetic bone substitute, is sometimes delivered into the bone cavity and allowed to set to a hardened condition to provide internal structural support to the bone.

An example of a balloon-expanding device is U.S. Pat. No. 6,127,597 to Beyar et al., which describes a bone fixture for insertion through the bore of a bone and into the intramedullary cavity. The bone fixture includes a diameter-expandable, metallic balloon tube having an exterior circumferential surface. The tube has a reduced first diameter for insertion through the bore and into the intramedullary cavity and a second expanded diameter, wherein when fluid is introduced into said bone fixture it radially increases in diameter from the reduced first diameter to the second expanded diameter.

However, it has been found that expansion of the balloon-like device is not readily controllable. Instead, when such balloon-like device is inflated, expansion occurs along a path of least resistance. As a result, the direction of compaction of the cancellous bone and/or reduction of the compression fracture is not controllable, and expansion occurs in multiple directions and along multiple axes.

Another device for treatment of the spine is described in U.S. Pat. No. 6,676,665 to Foley et al. This device includes an elongate member having a deformable distal end portion at least partially formed of a flexible and preferably elastic material. The distal end portion has an initial configuration for placement adjacent a vertebral body and a deformed configuration defining at least one outwardly extending projection for displacement of at least a portion of the vertebral body. The elongate member preferably comprises a rod member, a sleeve member and an actuator mechanism for imparting relative linear displacement between the rod and sleeve members to effect outward deformation of the distal end portion of the sleeve member. In one embodiment, the instrumentation is used to compact cancellous bone to form a cavity within a vertebral body. In another embodiment, the instrumentation is used to reduce a compression fracture. In yet another embodiment, the instrumentation is used to distract a disc space between adjacent vertebral bodies.

U.S. Pat. No. 6,554,833 to Levy et al. describes a device for stabilizing bone, which includes a tubular body having first and second end regions defining a longitudinal axis therebetween. A plurality of splines extend from the first end region, the splines including first ends coupled to the first end region, and second ends disposed away from the first end region, the second ends being directable from a generally axial collapsed state to a substantially transverse expanded state. A plurality of support arms are coupled to the splines, and an actuator is coupled to the support arms, the actuator movable axially relative to the elongate body for causing the support arms to direct the second ends of the splines from the collapsed state to the expanded state. Optionally, the device includes another set of splines extending from the second end region or located at an intermediate region of the tubular body.

SUMMARY OF THE INVENTION

The present invention seeks to provide an expandable bone device, as is described in detail further hereinbelow. The expandable bone device of the invention may be described hereinbelow for use with the spine (e.g., the pedicles or spine processes and the like), but it is emphasized that the invention is not limited to the spine, and may be used for any bone, such as but not limited to, calcaneous, distal radius, upper tibia, hands bones and bone epiphysis. The invention may be used in the treatment of any bone disease, disorder or problem, such as but not limited to, fractures, prevention of trauma or fractures due to osteoporosis, endocrine, metabolic or tumoral bone diseases, AVN and trauma. The invention may be used as "scaffolding" to support bone structures, such as for filling bone structures (e.g., with cement, bone graft, bone substitutes or collagen and other materials), and may or may not be left in the bone structure, depending on the procedure used.

There is thus provided in accordance with an embodiment of the present invention an expandable bone device including a unitary body extending along a longitudinal axis and including a deformable distal end portion having a collapsed orientation for placement adjacent a spinal structure, the deformable distal end portion including relatively wide, mutually contiguous support surfaces outlined by relatively narrow cutouts, the support surfaces being contiguous with the rest of the unitary body via relatively narrow deformable splines, the deformable distal end portion having an expanded orientation wherein the support surfaces are moved transversely outwards away from and generally parallel to the longitudinal axis, and an actuator coupled to the deformable distal end portion and operative to cause movement of the deformable distal end portion between the collapsed orientation and the expanded orientation.

The expandable bone device may include one or more of the following features. For example, the support surfaces may be arranged in one or more pairs of support surfaces that expand transversely outwards in opposite directions symmetrically or non-symmetrically with respect to the longitudinal axis. Some of the narrow cutouts may be generally parallel to the longitudinal axis. Additionally or alternatively, some of the narrow cutouts may be angled at a non-zero angle with respect to the longitudinal axis. The deformable splines may be generally equally spaced or are spaced at different distances from one another along the longitudinal axis.

The unitary body may be generally cylindrical in shape. Alternatively, the unitary body may include a generally flat polygonal shape folded about a fold axis generally transverse to the longitudinal axis.

A bridge element may connect between two of the unitary bodies. The deformable distal end portion may include at least one non-smooth surface adapted to adhere to a spinal structure. The unitary body may include a non-deformable endpiece distal to the deformable distal end portion.

BRIEF DESCRIPTION OF THE DRAWINGS

The present invention will be understood and appreciated more fully from the following detailed description taken in conjunction with the drawings in which:

FIGS. 5A, 5B and 5C are simplified pictorial illustrations of an expandable bone device, constructed and operative in accordance with yet another embodiment of the present invention, respectively, in collapsed, semi-expanded and fully expanded orientations;

FIG. 6A is a simplified pictorial illustration of an expandable bone device, constructed and operative in accordance with still another embodiment of the present invention, in a collapsed orientation, and including a non-deformable endpiece distal to the deformable distal end portion;

FIG. 6B is a simplified pictorial illustration of an expandable bone device, constructed and operative in accordance with another embodiment of the present invention, in a collapsed orientation, and without the non-deformable endpiece;

DETAILED DESCRIPTION OF EMBODIMENTS

Figure 1:
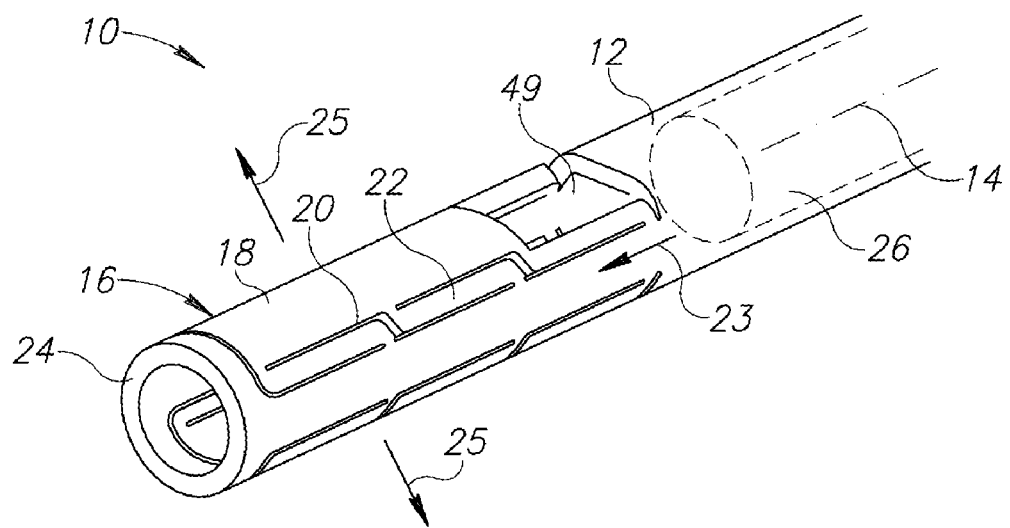
FIG. 1 is a simplified pictorial illustration of an expandable bone device, constructed and operative in accordance with an embodiment of the present invention, in a collapsed orientation, and including a non-deformable endpiece distal to a deformable distal end portion.

Reference is now made to FIG. 1, which illustrates an expandable bone device 10, constructed and operative in accordance with an embodiment of the present invention.

The expandable bone device 10 may include a unitary body 12 extending along a longitudinal axis 14. Device 10 may include a deformable distal end portion 16 having a collapsed orientation for placement adjacent a spinal structure. The deformable distal end portion 16 may include relatively wide, mutually contiguous support surfaces 18 outlined by relatively narrow cutouts 20. The support surfaces 18 are contiguous with the rest of the unitary body 12 via relatively narrow deformable splines 22.

In the illustrated, non-limiting embodiment of FIG. 1, unitary body 12 may be generally cylindrical in shape (although any other shape is also in the scope of the invention) and may include a non-deformable endpiece 24 distal to the deformable distal end portion 16. The non-deformable endpiece 24 may be a ring contiguous with the rest of the unitary body 12. One or more of the support surfaces 18 may be non-smooth for enhancing adhesion to spinal structure. Additionally or alternatively, one or more of the support surfaces 18 may be coated with a material that enhances adhesion with bone, such as but not limited to, hydroxyapatite. The support surfaces in the illustrated embodiments are arcuate (following the contour of the cylindrical shape) but may be any other shape and size as well.

The expandable bone device 10 may be constructed, without limitation, of medically safe metals (e.g., stainless steel, shape memory alloys, such as NITINOL) or plastics, including resorbable materials and shape memory polymers.

As seen in FIG. 1, some of the narrow cutouts 20 may be generally parallel to the longitudinal axis 14. Additionally or alternatively, some of the narrow cutouts 20 may be angled at a non-zero angle with respect to the longitudinal axis 14. The deformable splines 22 may be generally equally spaced or are spaced at different distances from one another along the longitudinal axis 14.

Figure 2:
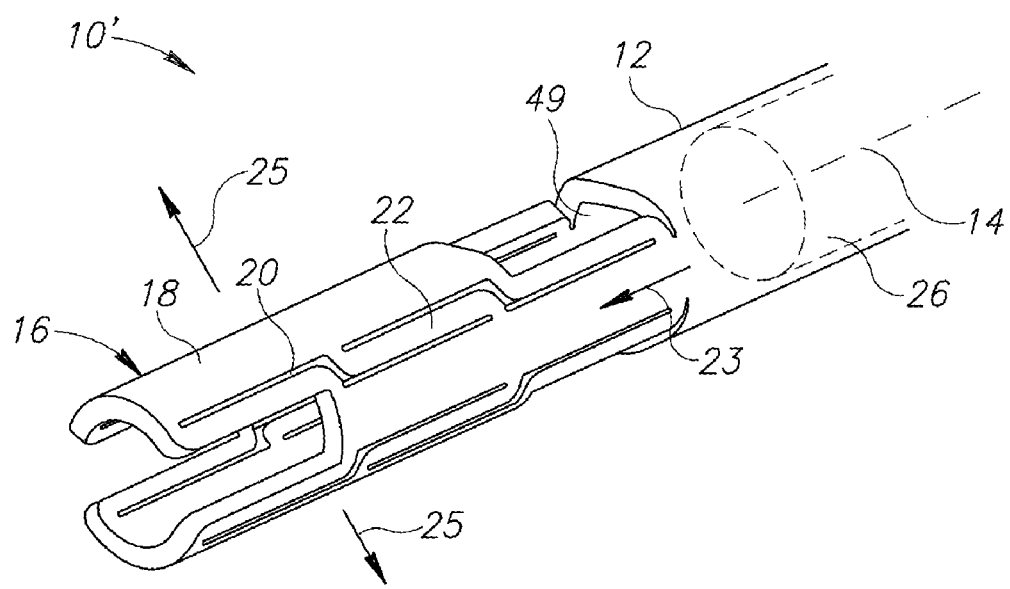
FIG. 2 is a simplified pictorial illustration of an expandable bone device, constructed and operative in accordance with another embodiment of the present invention, in a collapsed orientation, and without the non-deformable endpiece.

FIG. 1 illustrates a version of the expandable bone device 10 including the endpiece 24. FIG. 2 illustrates another non-limiting version of expandable bone device 10, referred to as expandable bone device 10', without the non-deformable endpiece 24. Both FIGS. 1 and 2 illustrate the expandable bone device in a collapsed orientation.

Figure 3A:
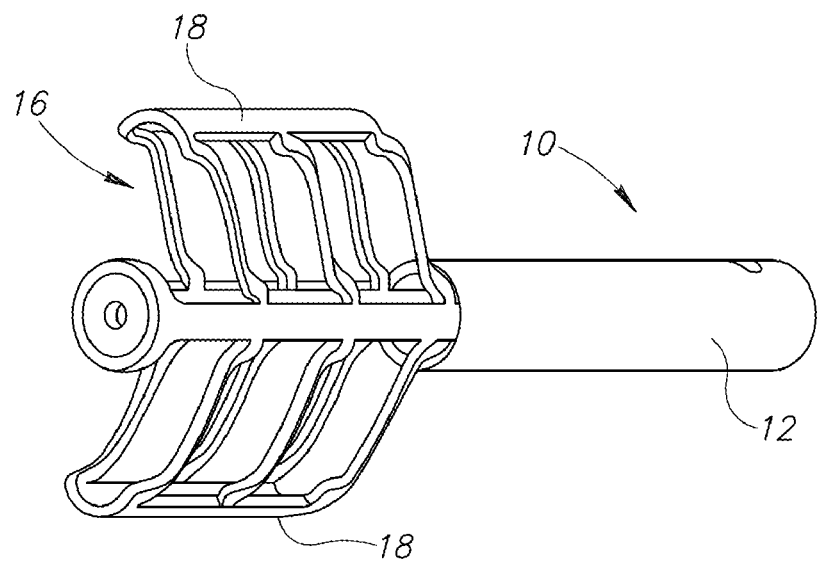
FIG. 3A is a simplified pictorial illustration of the expandable bone device of FIG. 1 in an expanded orientation.
Figure 3B:
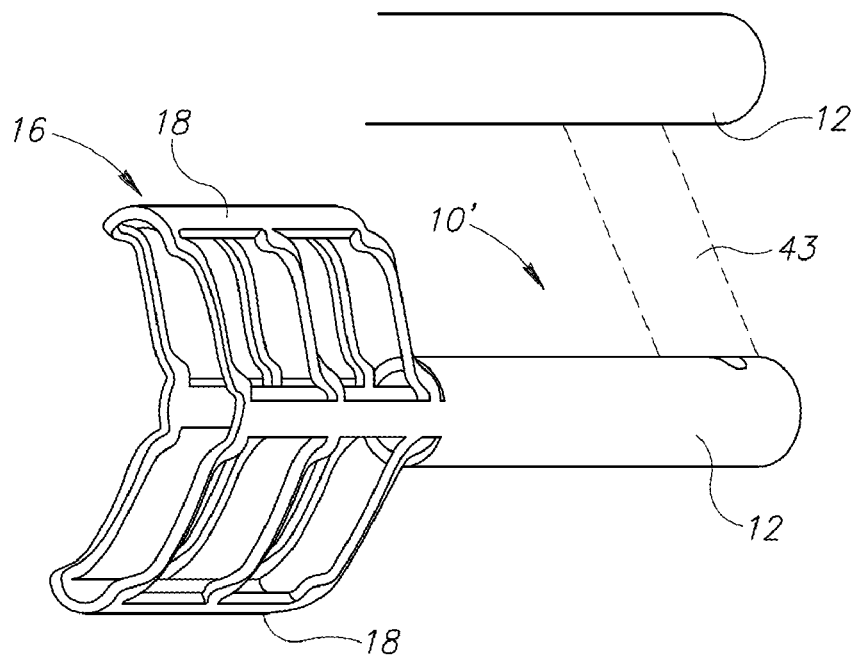
FIG. 3B is a simplified pictorial illustration of the expandable bone device of FIG. 2 in an expanded orientation.

An actuator 26 may be coupled to the deformable distal end portion 16. The actuator 26 may effect movement of the deformable distal end portion 16 between the collapsed orientation and the expanded orientation. Without limitation, the actuator 26 may be similar to the actuator (also referred to as the elongate control member) shown and described with reference to the embodiment of FIGS. 12-15D in U.S. Pat. No. 6,554,833. For example, the actuator 26 may be a threaded rod that mates with internal threads formed in the unitary body 12. Rotation of the threaded rod may advance the rod distally towards the deformable distal end portion 16, as indicated by arrow 23. The threaded rod wedges into the deformable distal end portion 16 and causes the support surfaces to move transversely outwards away from and generally parallel to the longitudinal axis 14, as indicated by arrows 25, to an expanded orientation. FIG. 3A and FIG. 3B illustrate the expandable bone devices 10 and 10', respectively, in the expanded orientations.

It is emphasized that the invention is not limited to the above-described actuator 26 and other ways of expanding the deformable distal end portion 16 may be used to carry out the invention as well, such as but not limited to, mechanical (manual or motorized), pneumatic, hydraulic or any other expansion method.

As seen in FIGS. 3A and 3B, the support surfaces 18 may be arranged in one or more pairs that expand transversely outwards in opposite directions symmetrically or non-symmetrically with respect to the longitudinal axis 14. For symmetrical expansion, the lengths of the deformable splines 22 may be equal. For non-symmetrical expansion, the lengths of the deformable splines 22 may be different, making possible expansion at different or variable angles relative to the longitudinal axis 14. Additionally or alternatively, deformable distal end portion 16 with its support surfaces 18 may be deformed into different non-straight shapes (e.g., a wedge shape, a concave shape, a convex shape, etc.) by making the length of the deformable splines 22 gradually higher from their proximal end to their distal end or vice-versa.

Figure 4A:
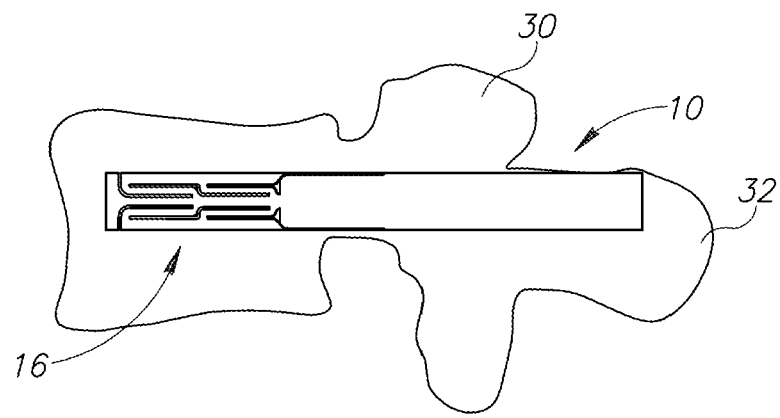
FIGS. 4A, 4B and 4C are simplified pictorial illustrations of the expandable bone device of FIG. 1, introduced into a vertebral body through a pedicle, respectively, in collapsed, semi-expanded and fully expanded orientations.
Figure 4B:
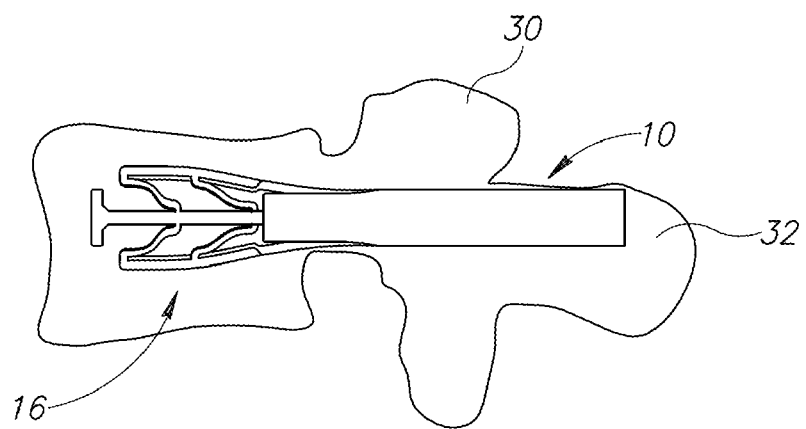
Figure 4C:
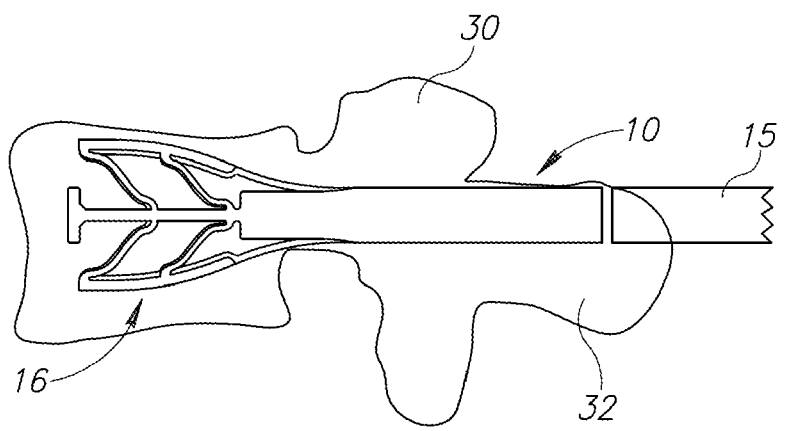

Reference is now made to FIGS. 4A, 4B and 4C, which illustrate that the expandable bone device 10 may be gradually expanded and contracted in a controlled manner. FIG. 4A illustrates introducing into the expandable bone device 10 into a vertebral body 30 through a pedicle 32. This is a well known approach used in spinal surgery called the transpedicular approach, commonly used for introducing pedicle screws and for performing vertebroplasty with a balloon or a cannula, such as for filling the spinal body with bone cement or other materials.

FIG. 4B illustrates the expandable bone device 10 in a semi-expanded orientation. FIG. 4C illustrates the expandable bone device 10 in a fully expanded orientation. The expansion is reversible and can be reversed for removal by collapsing the device in situ with the actuator 26 or other tool. The expanded state can be locked.

A bridge element 43 (FIG. 3B) may be used to connect two unitary bodies 12 together. The bridge element 43 may be situated in the posterior area of the vertebra while the expanded device 10 is inside the vertebral body (anterior aspect of the vertebra). Any number of expandable bone devices 10 (not just one) may be introduced into the vertebral body or other bone.

Reference is now made to FIGS. 5A, 5B and 5C, which illustrate an expandable bone device 50, constructed and operative in accordance with yet another embodiment of the present invention, respectively, in collapsed, semi-expanded and fully expanded orientations. Whereas in the embodiments of FIGS. 1 and 2 there are three deformable splines 22 for each support surface 18, in the embodiments of FIGS. 5A-5C there are two deformable splines 52 for each support surface 18. Any number of deformable splines may be used in the present invention. In the embodiments of FIGS. 1 and 2, the proximal ends of the support surfaces 18 are separated by a gap 49 from the rest of the unitary body 12. In the embodiments of FIGS. 5A-5C, there is no such gap.

Reference is now made to FIG. 6A is a simplified pictorial illustration of an expandable bone device 60, constructed and operative in accordance with still another embodiment of the present invention, in a collapsed orientation.

Figure 7A:
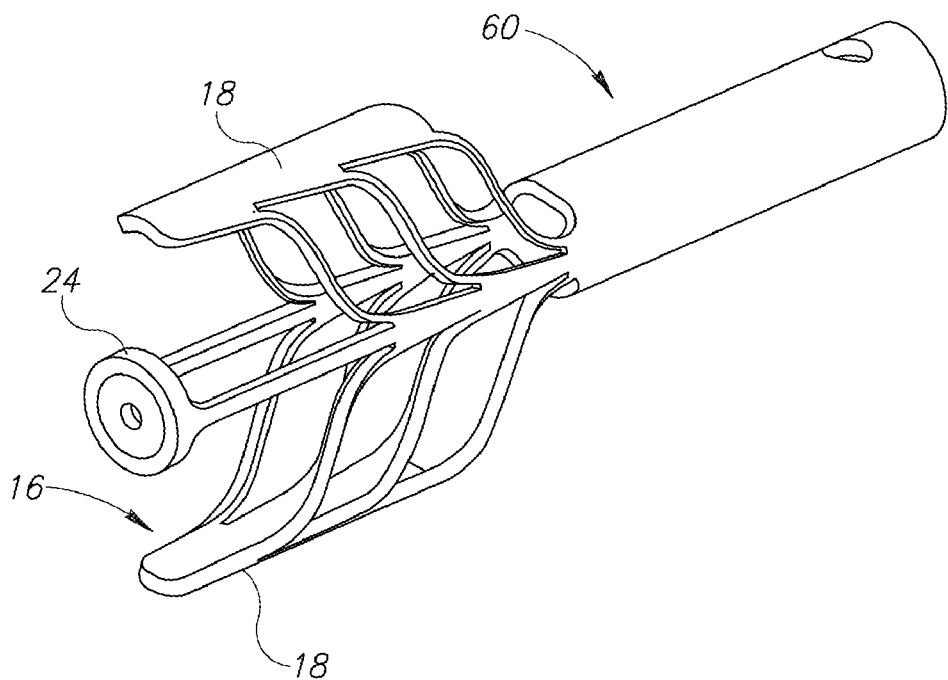
FIG. 7A is a simplified pictorial illustration of the expandable bone device of FIG. 6A in an expanded orientation.
Figure 7B:
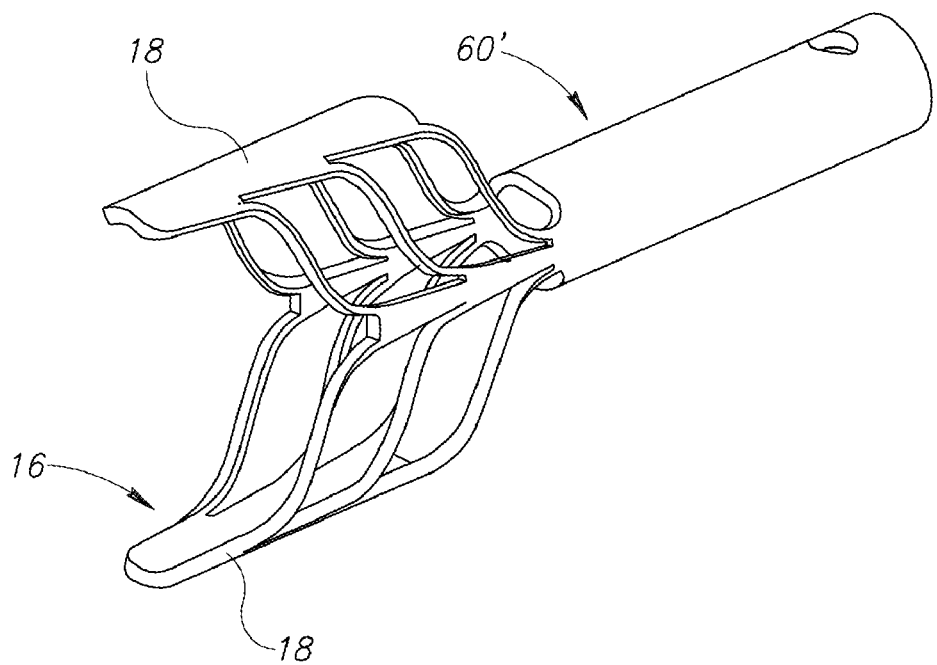
FIG. 7B is a simplified pictorial illustration of the expandable bone device of FIG. 6B in an expanded orientation.

The expandable bone device 60 is similar to the expandable bone device 10, with like elements being designated by like numerals. In expandable bone device 60, there are narrow cutouts 62 angled at a non-zero angle with respect to the longitudinal axis 14. FIG. 6B illustrates another non-limiting version of expandable bone device 60, referred to as expandable bone device 60', without the non-deformable endpiece 24. Both FIGS. 6A and 6B illustrate the expandable bone device in a collapsed orientation. FIGS. 7A and 7B illustrate the expandable bone devices 60 and 60', respectively, in an expanded orientation.

Figure 8:
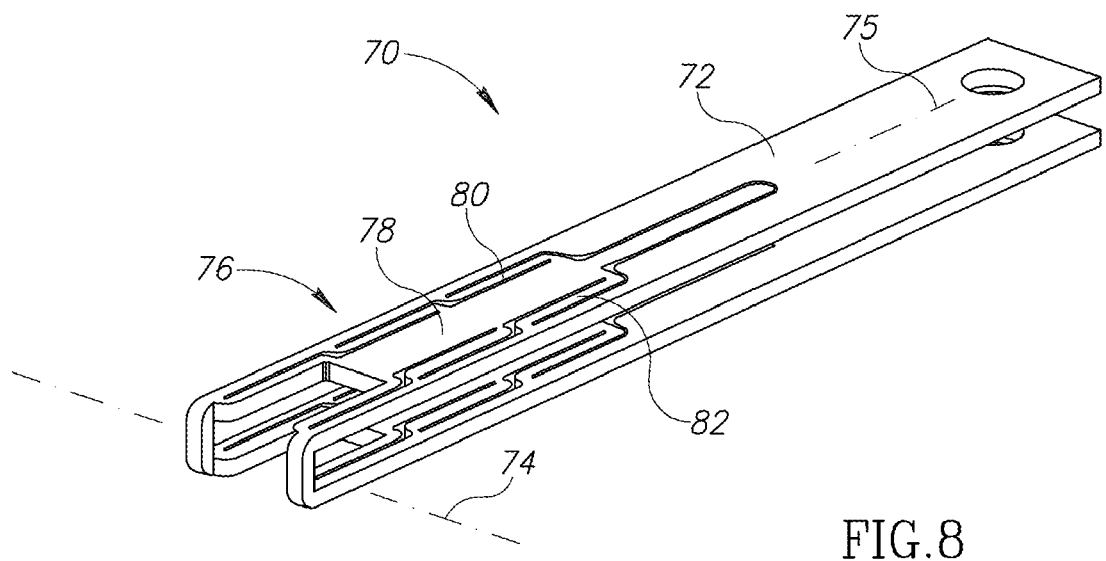
FIG. 8 is a simplified pictorial illustration of an expandable bone device, constructed and operative in accordance with still another embodiment of the present invention, in a collapsed orientation.

Reference is now made to FIG. 8, which illustrates an expandable bone device 70, constructed and operative in accordance with still another embodiment of the present invention, in a collapsed orientation. The expandable bone device 70 may be constructed of a unitary body 72 that has a generally flat polygonal shape (e.g., rectangular) folded about a fold axis 74 generally transverse to a longitudinal axis 75. Device 70 may include a deformable distal end portion 76 having a collapsed orientation for placement adjacent a spinal structure. The deformable distal end portion 76 may include relatively wide, mutually contiguous support surfaces 78 outlined by relatively narrow cutouts 80. The support surfaces 78 are contiguous with the rest of the unitary body 72 via relatively narrow deformable splines 82. An actuator (not shown) may be coupled to the deformable distal end portion 76 for moving the deformable distal end portion 76 between the collapsed orientation and the expanded orientation, as similarly described hereinabove.

Figure 9A:
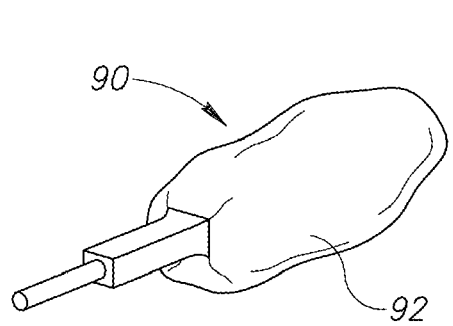
FIGS. 9A, 9B, 10A and 10B are simplified pictorial illustrations of expandable bone devices, constructed and operative in accordance with other embodiments of the present invention, wherein the devices expand to prismatic shapes, respectively shown in contracted (FIGS. 9A and 10A) and expanded (FIGS. 9B and 10B) orientations.
Figure 9B:
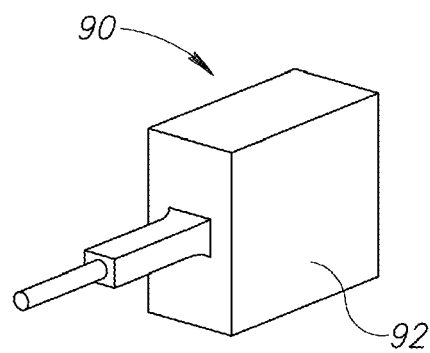
Figure 10A:
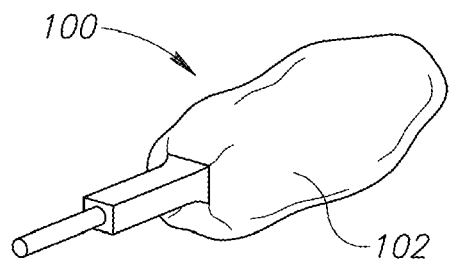
Figure 10B:
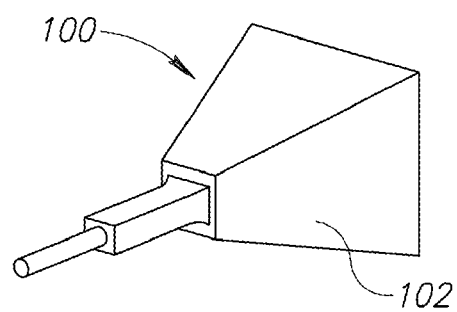

Reference is now made to FIGS. 9A and 9B, and 10A and 10B, which illustrate expandable bone devices 90 and 100, constructed and operative in accordance with other embodiments of the present invention. The expandable bone devices 90 and 100 may be constructed like stents, such as but not limited to, braided stents (filaments or wires, wound or braided into a particular configuration), or mesh stents (metal mesh bent or formed into a particular shape), among others (e.g., struts or other shapes and kinds of connecting elements). As is typical with stents, the expandable bone devices 90 and 100 may have a deformable portion 92 (102, respectively) with a compressed (e.g., collapsed, deformed, deflated or contracted) orientation (FIGS. 9A and 10A, respectively) which may be expanded to an expanded orientation (FIGS. 9B and 10B, respectively). The expansion may be effected by spring elasticity, balloon or mechanical expansion, or by the self-expansion of a thermally or stress-induced return of a shape memory alloy (such as a nickel-titanium alloy, e.g., NITINOL) to a pre-conditioned expanded configuration.

In accordance with non-limiting embodiments of the present invention, the devices 90 and 100 expand to prismatic shapes. For example, the device 90 may expand to a three-dimensional rectangular prismatic shape. The device 100 may expand to a three-dimensional trapezoidal shape. These are just two non-limiting examples, and the invention is not limited to any particular shape.

In the collapsed state of FIGS. 9A and 10A, the device may be introduced through the pedicles, such as with a sheath or catheter, as is known with stents. The device may be useful, for example, for treating fractures (wherein no large size reduction is required) or for preventive treatment of weak non-fractured vertebras.

Figure 11A:
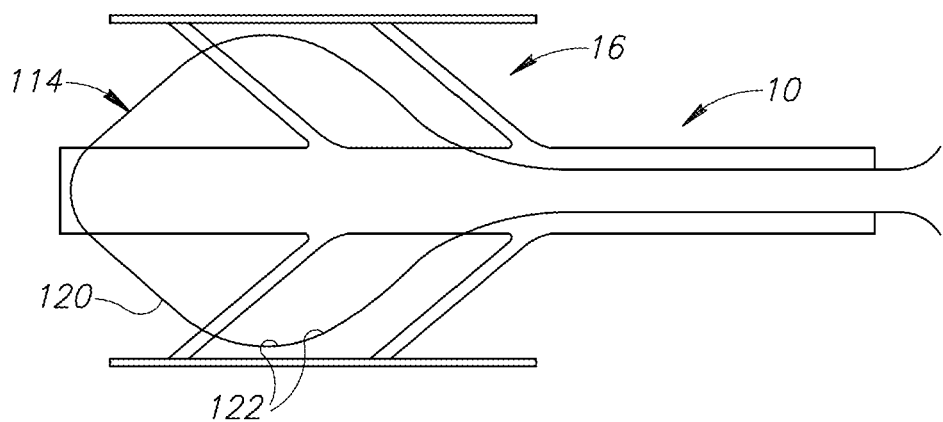
FIGS. 11A, 11B and 11C are pictorial illustrations of the expandable bone device of FIG. 1 with different actuators that may move the deformable distal end portion between collapsed and expanded orientations, in accordance with different embodiments of the present invention.
Figure 11B:
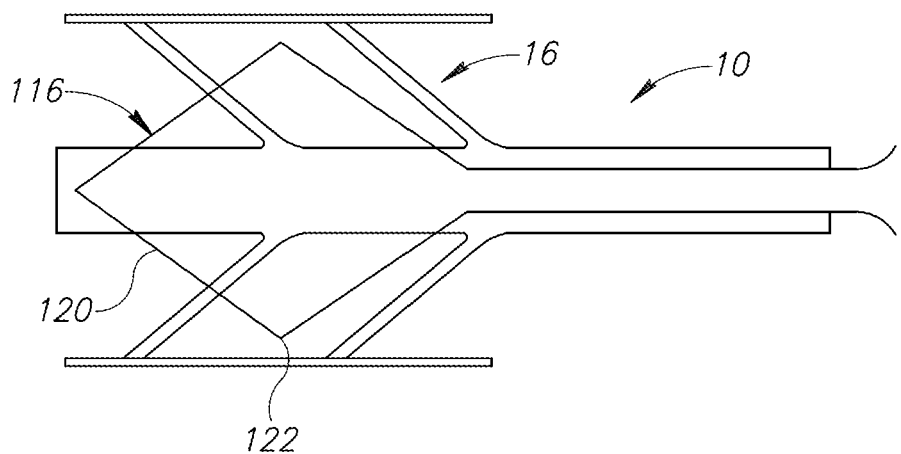
Figure 11C:
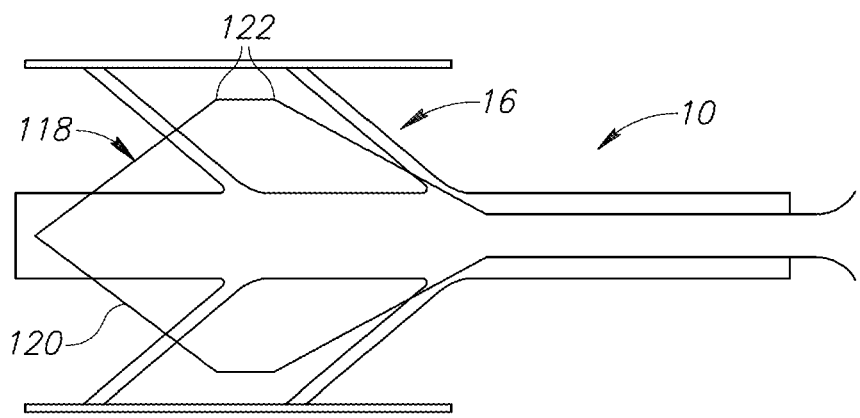

Reference is now made to FIGS. 11A, 11B and 11C, which illustrate the expandable bone device 10 with different actuators (structures 114, 116 and 118, respectively) that may be coupled to the deformable distal end portion 16 to cause movement of the deformable distal end portion 16 between the collapsed orientation and the expanded orientation, in accordance with embodiments of the present invention. It is noted that "coupled to" encompasses both mechanical direct and indirect linkage as well as non-mechanical coupling, such as but not limited to, electrical, hydraulic and pneumatic, for example. The expandable bone device 10 may be expanded by the actuator, and the actuator may be left in place to form support structure for the device 10. Alternatively, the expandable bone device 10 may be expanded to form a skeletal structure wherein the actuator is removed after expansion.

As another alternative, the structures 114, 116 and 118 may not be used as actuators, but rather as support structures. That is, the expandable bone device 10 may be expanded with some other actuator (not shown here) and the structures 114, 116 and 118 may be introduced into the expanded bone device 10 to provide extra support in situ.

In accordance with one embodiment of the invention, each actuator (or support structure) includes an elongate strip 120 with one or more score lines 122 about which the strip 120 can bend to take on different shapes and forms. For example, in FIG. 11A, the actuator (or support structure) has an arcuate expanded shape (e.g., oval spheroid shape). In FIG. 11B, the actuator (or support structure) has a polygonal shape (e.g., diamond shape). In FIG. 11C, the actuator (or support structure) has another polygonal shape (e.g., trapezoidal shape). The actuator may have any combination of these shapes or other shapes as well. The actuator (or support structure) may be made of the same or similar material as that of expandable bone device 10 but with different hardness, stiffness or other mechanical properties, or with different dimensions (e.g., thickness and wideness) and shape. The selection of different materials and properties allows different degrees of stiffness for the supporting structure and for the whole system that may be used for different bones, patient ages and body parameters that answer the needs for adequate fixation in each case. The actuators (or supporting structures) may be supplied in a stock of different pieces, so the practitioner can choose the best one for the job. They can be locked in place in many different ways.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:

1. An expandable bone device comprising:
a unitary body extending along a longitudinal axis and including a deformable distal end portion having a collapsed orientation for placement adjacent a bone structure, said deformable distal end portion comprising relatively wide, mutually contiguous support surfaces outlined by relatively narrow cutouts, said support surfaces being contiguous with the rest of the unitary body via relatively narrow deformable splines, said deformable distal end portion having an expanded orientation wherein said support surfaces are moved transversely outwards away from and generally parallel to the longitudinal axis, and wherein in the expanded orientation, distal ends of said support surfaces are disconnected and distanced from one another by an open gap; and
an actuator coupled to said deformable distal end portion and operative to cause movement of said deformable distal end portion between the collapsed orientation and the expanded orientation and wherein in the expanded orientation said deformable splines are misshapen as compared to the collapsed orientation.

2. The expandable bone device according to claim 1, wherein said support surfaces are arranged in at least one pair of support surfaces that expand transversely outwards in opposite directions with respect to the longitudinal axis.

3. The expandable bone device according to claim 2, wherein the at least one pair of support surfaces expand transversely outwards in opposite directions symmetrically with respect to the longitudinal axis.

4. The expandable bone device according to claim 2, wherein the at least one pair of support surfaces expand transversely outwards in opposite directions non-symmetrically with respect to the longitudinal axis.

5. The expandable bone device according to claim 1, wherein some of said narrow cutouts are generally parallel to the longitudinal axis.

6. The expandable bone device according to claim 1, wherein some of said narrow cutouts are angled at a non-zero angle with respect to the longitudinal axis.

7. The expandable bone device according to claim 1, wherein said deformable splines are generally equally spaced from one another along the longitudinal axis.

8. The expandable bone device according to claim 1, wherein at least some of said deformable splines are spaced at different distances from one another along the longitudinal axis.

9. The expandable bone device according to claim 1, wherein said unitary body comprises a generally flat polygonal shape folded about a fold axis generally transverse to the longitudinal axis.

10. The expandable bone device according to claim 1, further comprising a bridge element that connects between two of said unitary bodies.

11. The expandable bone device according to claim 1, wherein said deformable distal end portion comprises at least one non-smooth surface adapted to adhere to a bone structure.

12. The expandable bone device according to claim 1, wherein said unitary body comprises a non-deformable end-piece distal to said deformable distal end portion.

13. The expandable bone device according to claim 1, wherein said actuator comprises an elongate strip with at least one score line about which the elongate strip is bendable.

14. The expandable bone device according to claim 13, wherein said actuator has at least one of an arcuate expanded shape and a polygonal shape.

15. The expandable bone device according to claim 1, further comprising support structure that supports said deformable distal end portion, said support structure comprising an elongate strip with at least one score line about which the elongate strip is bendable.

* * * * *